(12) United States Patent
Markle

(10) Patent No.: US 11,360,066 B2
(45) Date of Patent: Jun. 14, 2022

(54) GAS PHASE STANDARD PREPARATION DEVICE AND METHOD TO USE

(71) Applicant: Doug Markle, Cumming, GA (US)

(72) Inventor: Doug Markle, Cumming, GA (US)

( * ) Notice: Subject to any disclaimer, the term of this patent is extended or adjusted under 35 U.S.C. 154(b) by 521 days.

(21) Appl. No.: 15/999,506

(22) Filed: Aug. 20, 2018

(65) Prior Publication Data

US 2020/0057040 A1 Feb. 20, 2020

(51) Int. Cl.
*G01N 33/00* (2006.01)
*G01N 1/22* (2006.01)
(Continued)

(52) U.S. Cl.
CPC .......... *G01N 33/0018* (2013.01); *G01N 1/22* (2013.01); *G01N 30/06* (2013.01); *G01N 30/30* (2013.01);
(Continued)

(58) Field of Classification Search
CPC .. G01N 33/0018; G01N 1/22; G01N 33/0073; G01N 30/06; G01N 30/74;
(Continued)

(56) References Cited

U.S. PATENT DOCUMENTS 3,760,773 A * 9/1973 Christensen ............... B01J 7/02
122/4 R
4,036,915 A * 7/1977 Lucero ..................... B01F 3/022
261/104

(Continued)

FOREIGN PATENT DOCUMENTS

EP          0500938 A1 *  9/1992  ............... G01N 1/34
WO   WO-2010072581 A *  7/2010  ......... G01N 33/0006
WO       2017180933 A1   10/2017

OTHER PUBLICATIONS

Platonov, I A et al. "Methods and Devices for the Preparation of Standard Gas Mixtures." Journal of analytical chemistry (New York, N.Y.) 73.2 (2018): 109-127. Web. (Year: 2018).*

(Continued)

*Primary Examiner* — Benjamin R Whatley
*Assistant Examiner* — Curtis A Thompson
(74) *Attorney, Agent, or Firm* — Marks Gray, P.A.; Mitchell Ghaneie; Claire Patton

(57) ABSTRACT

This invention is a gas standard preparation device and method of use for creating a reference material or a certified reference material. The reference material or the certified reference material is used to quantitate air from a collected sample. This is beneficial for identifying if the air within the area contains certain volatile compounds or other undesired compounds. This is accomplished by providing a sealed ampule containing reference material that is eventually broken by the gas preparation device. Once the ampule is broken, the reference material within the ampule is mixed with a diluent gas and forced into a reference material cylinder. The concentration of the final reference material within the reference material cylinder is verified for use in testing collected air sample. Accordingly, this device allows for creating a custom reference material onsite in a laboratory without the need for shipping in pre-made compressed gas cylinders for air quality testing.

20 Claims, 7 Drawing Sheets

(51) Int. Cl.
*G01N 30/30* (2006.01)
*G01N 30/06* (2006.01)
*G01N 30/74* (2006.01)
*G01N 30/62* (2006.01)

(52) U.S. Cl.
CPC ......... *G01N 30/74* (2013.01); *G01N 33/0006* (2013.01); *G01N 33/0073* (2013.01); *G01N 2030/625* (2013.01)

(58) Field of Classification Search
CPC ............. G01N 30/30; G01N 2030/625; G01N 2001/2893; G01N 33/0006
See application file for complete search history.

(56) References Cited

U.S. PATENT DOCUMENTS

| | | | | |
|---|---|---|---|---|
| 4,142,860 | A * | 3/1979 | Mayeaux | B01F 3/02 137/557 |
| 5,457,983 | A * | 10/1995 | Sauvageau | G01N 33/0006 73/1.03 |
| 5,650,560 | A | 7/1997 | Troost | |
| 6,234,001 | B1 * | 5/2001 | Sorensen | G01N 33/0006 73/1.04 |
| 2018/0021466 | A1 * | 1/2018 | Shomali | A01N 59/00 422/29 |

OTHER PUBLICATIONS

Barratt, R. S. "The Preparation of Standard Gas Mixtures. A Review." Analyst (London) 106.1265 (1981): 817-. Web. (Year: 1981).*

* cited by examiner

US 11,360,066 B2

GAS PHASE STANDARD PREPARATION DEVICE AND METHOD TO USE

BACKGROUND OF THE INVENTION

This invention relates to preparing a reference material or a certified referential material, which is to be used for identifying and quantifying certain gaseous compounds in collected air samples. Commercial companies (such as Linde and Air Gas) and National Institute of Standards and Technology (NIST) provide premade standardized compounds, also known generally as "reference materials" or "certified reference materials", that are used for comparison with an air sample. In the art, the phrase "reference materials" may be used to refer generally to either or both of "uncertified" reference materials or certified reference materials. Once the air sample is compared to the reference material, the tested-for volatile compounds are then quantitated accordingly. However, the current system for providing standardized testing in laboratories becomes problematic when a lab requires a different concentration than those provided by Air Gas or Linde or NIST. Additionally, the current system requires shipment of high pressure cylinders which requires special shipping methods. In the current system, when the pressurized cylinders have reached their expiration date, they either need to be shipped back to the supplier for recertification or disposed of, both of which creates complications for laboratories. In other words, as technology advances and labs require different concentrations of reference materials, the invention described and claimed herein allows such labs to create a desired reference material at the desired concentration onsite and avoid the complications of sending and receiving certified pressurized cylinders.

BRIEF SUMMARY OF THE INVENTION

The gas phase standard preparation device described herein allows laboratories to request a custom reference material or a custom certified reference material for the requested air quality analysis. This is accomplished by providing a premade sealed ampule that contains the requested ampule reference material, which is comprised of a chemical cocktail at a pre-determined concentration. The ampule containing the ampule reference material is then placed into a bendable steel coated sleeve and the sleeve is sealed. The sleeve is then placed into a gas phase standard preparation station, which is comprised of three to four separate compartments. In a first embodiment the preparation station provides four compartments. In a second embodiment the preparation station provides three compartments. The first compartment provides two connections for a vacuum pump and for a diluent gas and several tubes that bring the diluent gas to a proportional valve and then a pressure sensor. Another tube is extended from the pressure sensor into a separate compartment and connected to the ampule sleeve which is placed in its own compartment. The ampule sleeve is then connected to an evacuated reference material cylinder which is placed in its own compartment.

The preparation station is further comprised of a first lid and a second lid. The first lid provides a mandrel that breaks the ampule in the sleeve when the first lid is closed. The second lid encloses the cylinder in its respective compartment. When the ampule containing the ampule reference material breaks from closure of the first lid, the nitrogen, which is used for dilution of the reference material concentration, pushes the ampule reference material from the ampule into the cylinder and fills the cylinder with the ampule reference material and the diluent to create the final reference material at a predetermined concentration.

NUMBER REFERENCES

5—Sealed ampule tube
10—Ampule
15—Ampule sleeve
20—Spacers
25—Compression fitting
40—Reference material cylinder
42—Shutoff valve
50—Preparation Station (First Embodiment)
50A—Housing
51—First lid
52—Second Lid
53—Clasp
54—Hinge
55—Vacuum pump
56—Vacuum pump valve
60—Diluent gas cylinder
61—Gas valve
64—Tube
65—Pressure sensor
66—gas/vacuum supply line
70—Mandrel
75—Lid Mandrel
80—Electronics control board
82—Power Source
83—AC Mains
84—Battery
85—Insulation wall
87—Bulkhead
90—Heat sink
100—Preparation Station (Second embodiment)
100A—Housing
105—Bearing
110—Load sensor
115—IR Sensor
120—Formed adapter

DETAILED DESCRIPTION OF THE EMBODIMENTS

This invention is for a device and method of use for a gas phase standard preparation device for providing a reference material or a certified reference material, which is to be used for identifying a specific gaseous compound or multiple gaseous compounds within a sample of air. This invention allows for the reference material or certified referential material to be created in a laboratory instead of ordering premade, high pressure cylinders that are to be utilized in the lab or at an off-site location. This invention additionally allows for the reference material or certified referential material to be tailored or customized for the lab that it is to be used in. This is beneficial when the companies that produce these reference materials or the National Institute of Standards and Technology (NIST) are incapable of providing a premade standardized reference material. This is also beneficial for the laboratory and the environment in the reduction of waste cylinders because the high-pressure cylinders may be reused. This invention would also result in drastically lower shipping costs due to the fact that a sealed ampule would be shipped as compared to a premade, high pressure cylinder.

Figure 1:
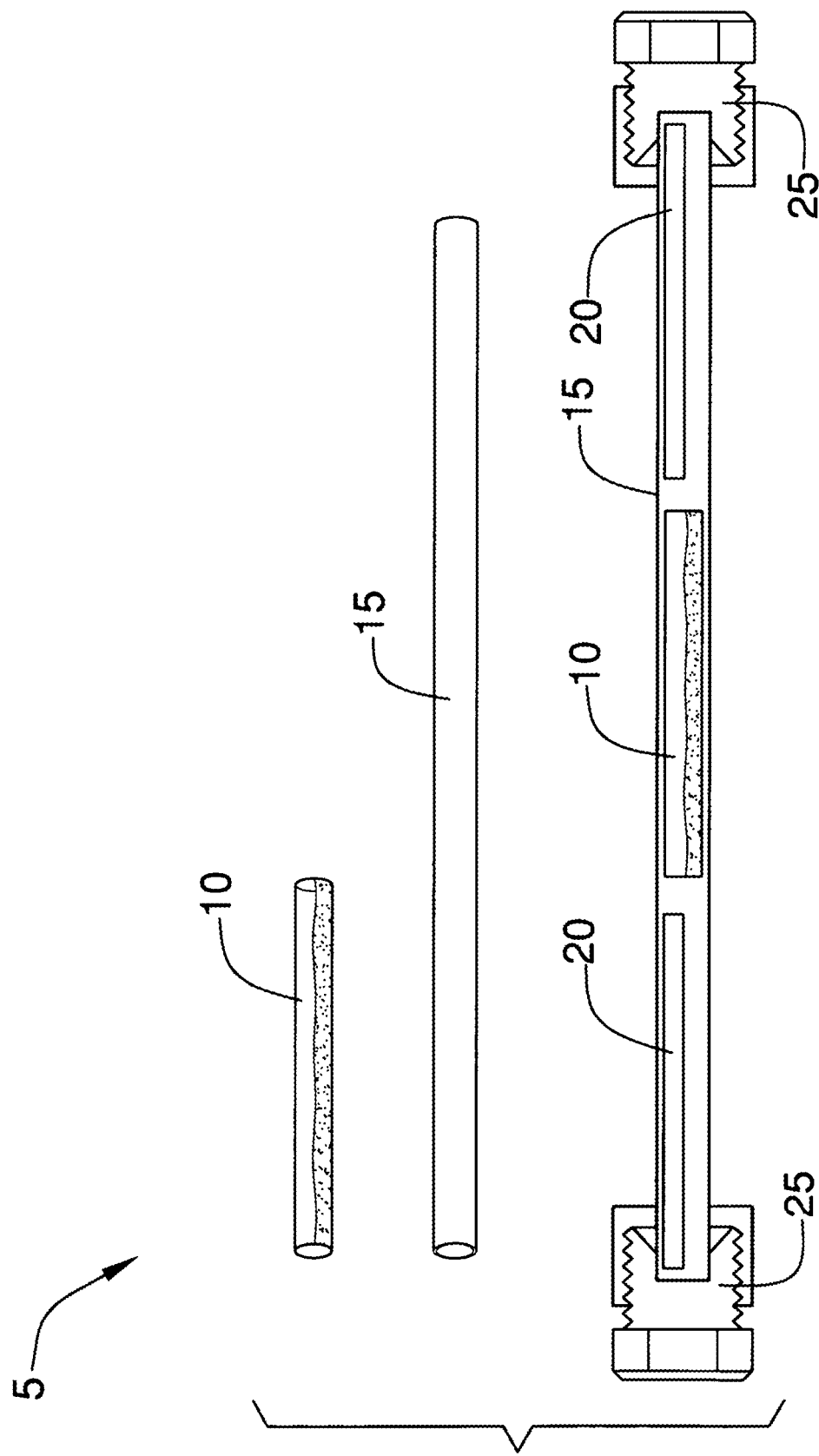
FIG. 1 shows the ampule sealed within the ampule sleeve prior to being placed into the gas phase standard preparation station.

This invention is comprised of a sealed ampule tube 5 which is comprised of an ampule 10, an ampule sleeve 15, and compression fittings 25 (with plugs). The ampule 10 contains a mixture of chemicals at predetermined concentrations, which collectively are referred to as ampule reference material. This ampule reference material will be mixed with diluent gas to form a final reference material which will be verified for concentration. The ampule 10 is placed within the ampule sleeve 15 and the ampule sleeve 15 should be made of air tight and inert or passivated materials. This is usually accomplished by providing a stainless steel sleeve internally coated with a passivation material such as a silica ceramic. The ampule sleeve 15 provides a first end and a second end with each end having a compression fitting 25, which can be seen in FIG. 1. While the ampule 10 is described as being made of glass, there could possibly be another material that the ampule is made from. It is anticipated that the sealed ampule tube 5 may also provide spacers 20 for maintaining the ampule 10 in a specific location within the ampule sleeve 15.

The ampule sleeve 15, which contains the ampule 10, is placed within a preparation station. The preparation station is described herein as two separate embodiments: a first embodiment 50 and a second embodiment 100. The first embodiment and second embodiment are described respectively below.

First Embodiment

Figure 2:
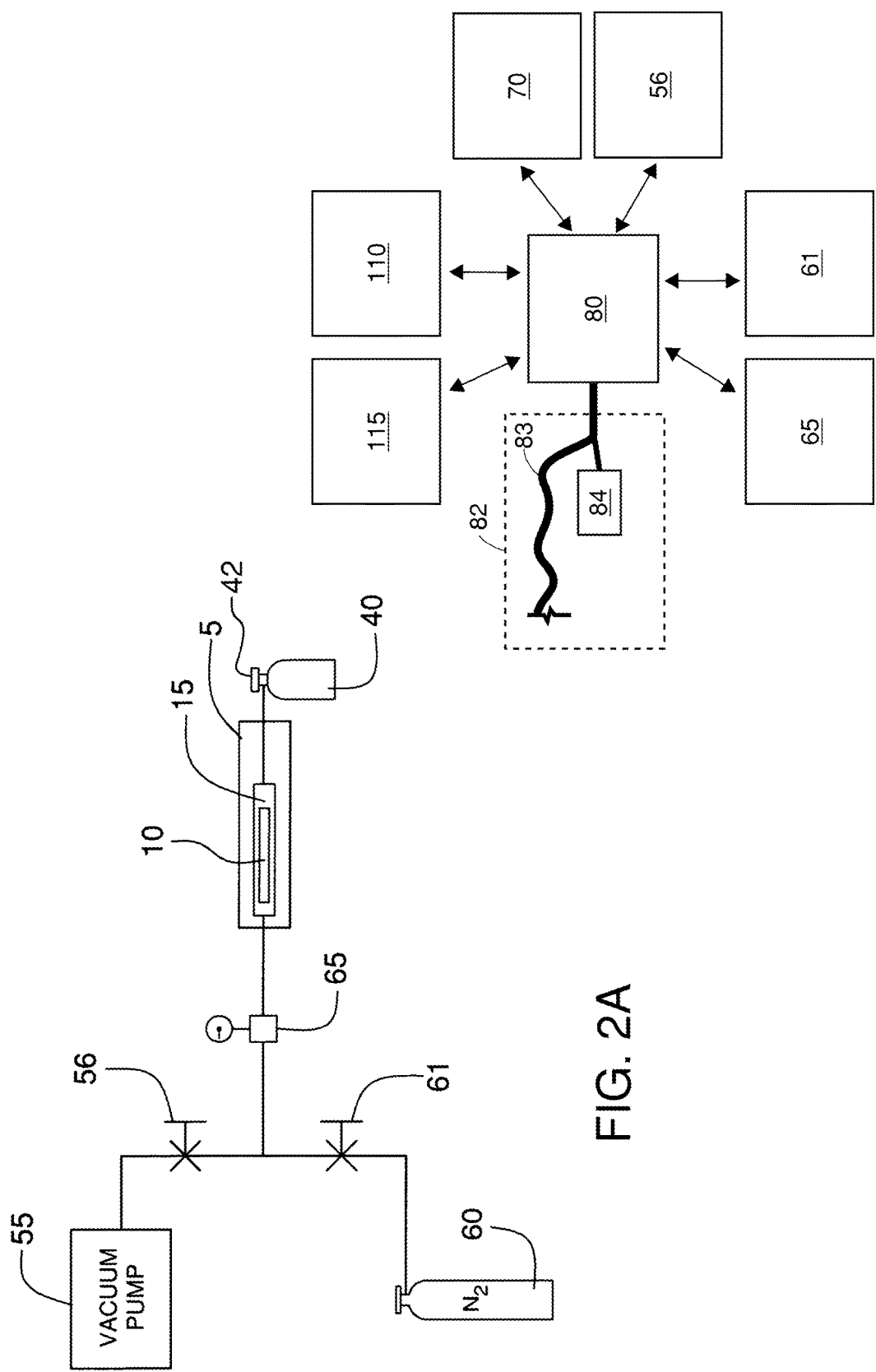
FIG. 2A is a schematic diagram of the preparation station.
FIG. 2B is a schematic diagram of the electric/electronic components of the preparation station.

This first embodiment 50 is a preparation station that is comprised of a housing 50A, sealed ampule tube 5, a first lid 51 with a clasp 53, a second lid 52, and a hinge 54 that the first lid 51 and second lid 52 are attached to, a heated mandrel 70, a lid mandrel 75, and an electronics control board 80. The electronics control board 80 of the gas phase standard preparation device is coupled to a power source 82, such as AC (alternating current) mains 83 or a battery 84 (see FIG. 2B). This embodiment is further comprised of a load sensor 110, an IR sensor 115, and a formed adapter 120. Although, the first embodiment 50 of the preparation station is shown and described as having four separate compartments, it is anticipated that the location, number, and orientation of the compartments may be altered without departing from the novel aspects of the invention being claimed and described herein.

Figure 3:
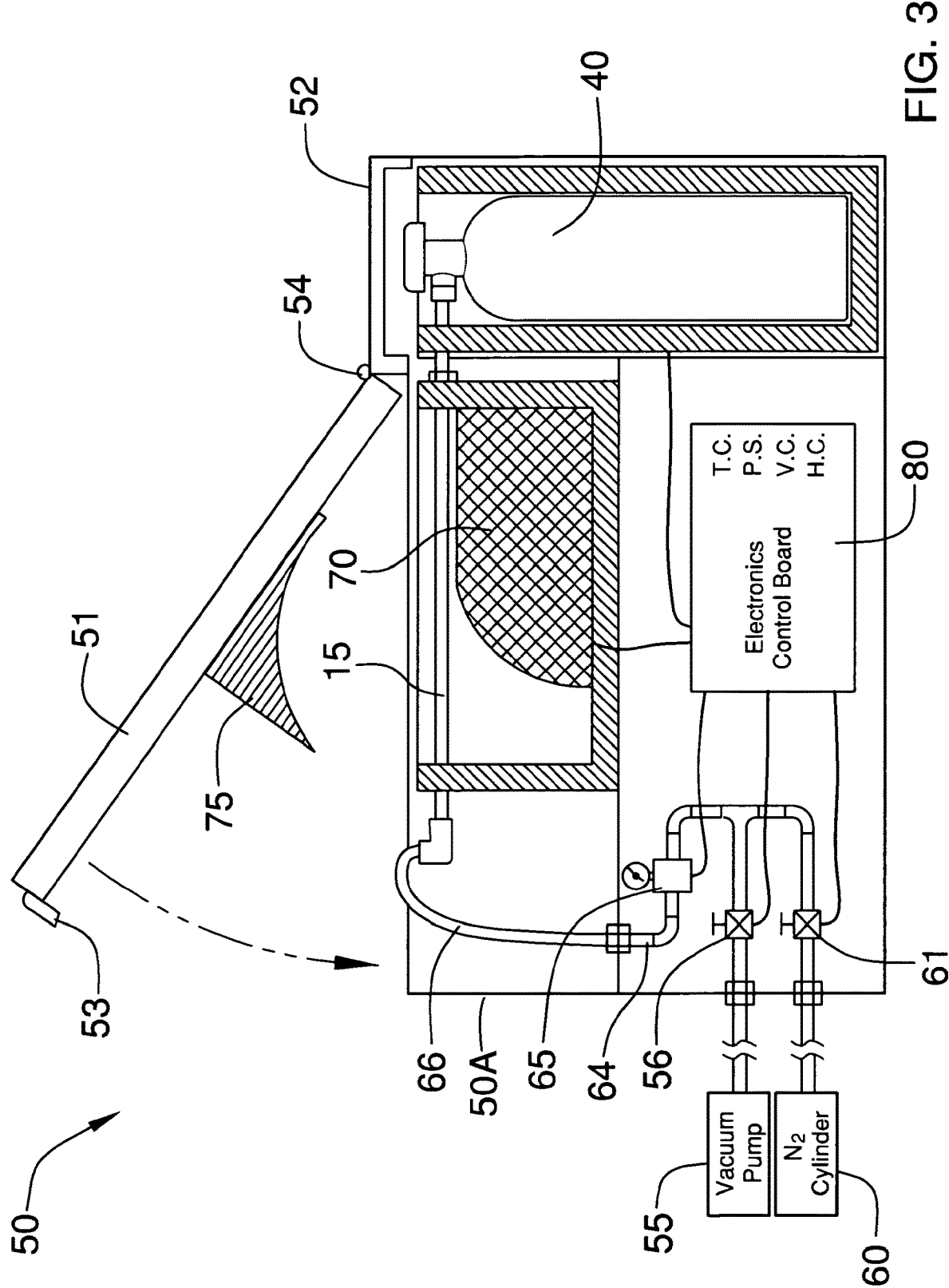
FIG. 3 shows a first embodiment of the preparation station with the first lid in an open position.
Figure 4:
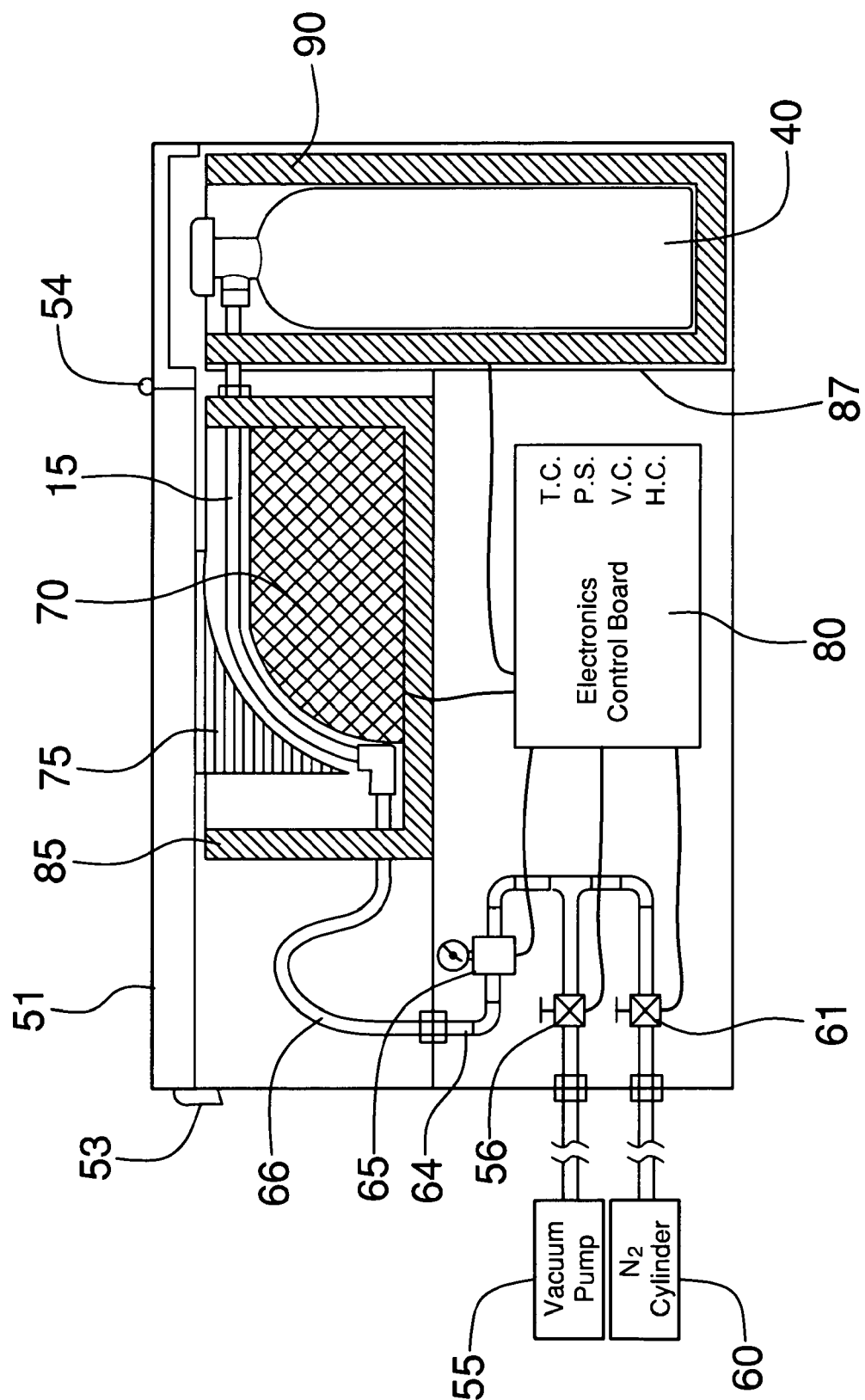
FIG. 4 shows the first embodiment of the preparation station with the first lid in a closed position.

The first compartment provides a first connection and a second connection in the exterior side of the housing for linking a vacuum pump 55 and diluent gas cylinder 60 respectively. Diluent gas cylinder 60 contains a suitable diluent gas, such as nitrogen gas. The vacuum pump 55 is connected to a vacuum pump valve 56 and the diluent gas cylinder 60 is attached to a diluent gas valve 61. A set of tubes extend from the vacuum pump valve 56 and the diluent gas valve 61 and converge into a tube 64 as seen in FIG. 3 and FIG. 4. The vacuum pump valve 56 and the diluent gas valve 61 are each proportional valves. The tube 64 connects to a pressure sensor 65. The tube 64 then extends from the pressure sensor 65 and links with a bendable gas supply line 66, which is provided in a second compartment as shown in FIG. 3 and FIG. 4.

The bendable gas supply line 66 is used to supply the diluent gas to the ampule sleeve 15 of sealed ampule tube 5 and also to remove any room air from within the ampule sleeve of the sealed ampule tube prior to supplying the diluent gas. The bendable gas supply line 66 has a first end and a second end. The first end of the bendable gas supply line 66 is linked to the tube 64 and the second end of the flexible gas supply line 66 is linked to the first end of the ampule sleeve 15 which contains the ampule 10.

The ampule sleeve 15 extends into a third compartment within the preparation station 50. The third compartment provides insulated walls 85 and the heated mandrel 70. The heated mandrel 70 provides heat at the location, or substantially at the location, of the ampule 10 within the ampule sleeve 15. The heated mandrel 70 is electrically linked and controlled by the electronics control board 80 in the first compartment. The second and third compartments within the preparation station 50 are adjacent to one another and are provided above the first compartment. The first lid 51 is provided above the second and third compartments, which is shown in FIG. 4. The first lid 51 provides access to the sealed ampule tube 15 for removal and installation.

The second end of the ampule sleeve 15 is linked to an evacuated reference material cylinder 40 with a formed adapter 120. The gas phase standard preparation device includes an interior bulkhead 87 attached to the housing that forms a fourth compartment. The reference material cylinder 40 is provided in the fourth compartment, receives the reference material or certified reference material, and includes a shutoff valve 42. A heat sink 90 is provided in the fourth compartments, which is accessible through the second lid 52. The heat sink 90 provides a level of security in the event that the integrity of the reference material cylinder 40 is compromised and also assists with absorbing heat as gas is compressed into the reference material cylinder 40. The insulation walls 85 are provided proximate to the heated mandrel 70 for conserving energy due to heat loss. When an individual desires to remove a reference material cylinder 40 or place a reference material cylinder 40 in the fourth compartment, the second lid 52 should be lifted.

A lid mandrel 75 is provided on the first lid 51. The lid mandrel 75 and heated mandrel 70 provide arcuate surfaces, which are shown in FIG. 3 and FIG. 4. The arcuate surface of the lid mandrel 75 compliments the arcuate surface of the heated mandrel 70. Accordingly, when the sealed ampule tube 5 is installed, the arcuate surface of the lid mandrel 75 will bend the ampule 10 within the sealed ampule tube 5 against the heated mandrel 70, thereby breaking the ampule and releasing the ampule reference material within it.

The electronics control board 80 is electronically linked to various electrical components within the gas standard preparation device as well as provides thermocouple control (T.C.), pressure sensor control (P.S.), valve control (V.C.), and heater control (H.C.). In the present invention the electronics control board 80 controls the IR sensor 115 thermocouple provided in the compartment housing the reference material cylinder 40. The electronics control board 80 also controls the pressure sensor 65, the vacuum pump valve 56, the diluent gas valve 61, and the heater control which is connected to the heated mandrel 70. In addition, it is anticipated that the lid mandrel 75 may provide heating elements and be electronically linked to the electronics control board 80. Electronics control board 80 is electronically linked with IR sensor 115 to allow for monitoring of the temperature of reference material cylinder 40 while being filled with gas, to prevent overheating, and with load sensor 110 for monitoring the weight of reference material cylinder 40 while it is being filled with gas, to determine the mass of gas being added.

The infrared ("IR") sensor 115 is provided to detect the temperature of the reference material cylinder 40 as it is being filled with gas. It is anticipated that the IR sensor 115 is electronically linked to the electronics control board 80 and assists with ensuring that the reference material cylinder 40 is not overheating due to compression of the gas filling the reference material cylinder.

The load sensor 110 is placed under the formed adapter 120. The formed adapter 120 is provided to link the sealed ampule tube 5 to the reference material cylinder 40. The formed adaptor 120 provides a fulcrum point of contact between the reference material cylinder 40 and the load sensor 110 to measure the mass of gas added to the cylinder 40. The formed adapter 120 is held down by the second lid 52, thereby causing the cylinder 40 to pull down as a cantilevered weight at the fulcrum point. Accordingly, an accurate weight can be observed as the cylinder 40 is filled.

The use of the formed adapter 120 and load sensor 110 in combination with the IR sensor 115 is significant because it avoids providing a weight sensor directly on each reference material cylinder 40 placed into the gas standard preparation device.

Prior to creating a reference material or a certified reference material with the preparation station 50, the second lid 52 is lifted, the reference material cylinder 40 is placed in the fourth compartment, the first lid 51 is lifted, and the sealed ampule tube 5 is installed in the preparation station. The sealed ampule tube 5 is installed by connecting the first end of sealed ampule tube 5 to the second end of the bendable gas supply line 66 and joining the second end of sealed ampule tube 5 to the reference material cylinder 40. A vacuum pump 55 is joined to the vacuum pump valve 56 and a diluent gas cylinder 60 filled with diluent gas is joined to the diluent gas valve 61. The vacuum pump 55 is used to remove any room air from the tubes and sealed ampule tube 5 within in the preparation station and perform a leak check. Once the room air is removed, the shutoff valve 42 of the reference material cylinder 40 is opened and a trickle flow of the diluent gas from the diluent gas cylinder 60 is released into the preparation station 50. Accordingly, the first lid 51 is closed, thereby breaking the ampule 10 and releasing the ampule reference material within the ampule 10 into the ampule sleeve 15. A preparation program is then started.

The preparation program is comprised of: (1) Heating the mandrel 70 to the desired temp up to 240 degrees Celsius; (2) Flowing the diluent gas through the ampule sleeve 15 containing the broken ampule 10 to mix the diluent gas with the ampule reference material as they flow into the reference material cylinder; (3) Monitor temperature on the reference material cylinder 40; (4) pressurize the cylinder to a final predetermined pressure; (4) Close the shutoff valve 42; and (5) Verify the concentration of the final reference material within the reference material cylinder.

Second Embodiment

Figure 5:
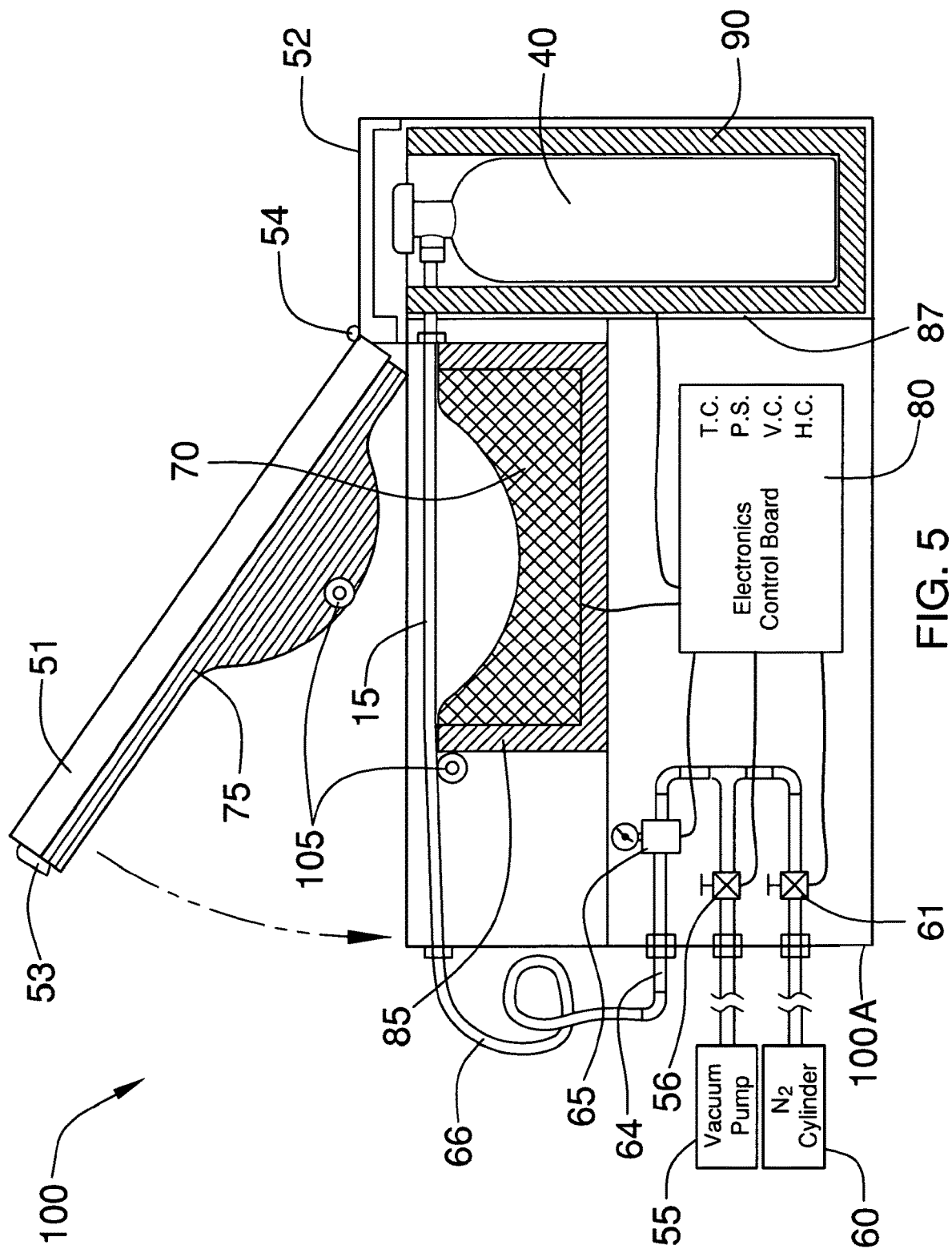
FIG. 5 shows a second embodiment of the preparation station with the first lid in an open position.
Figure 6:
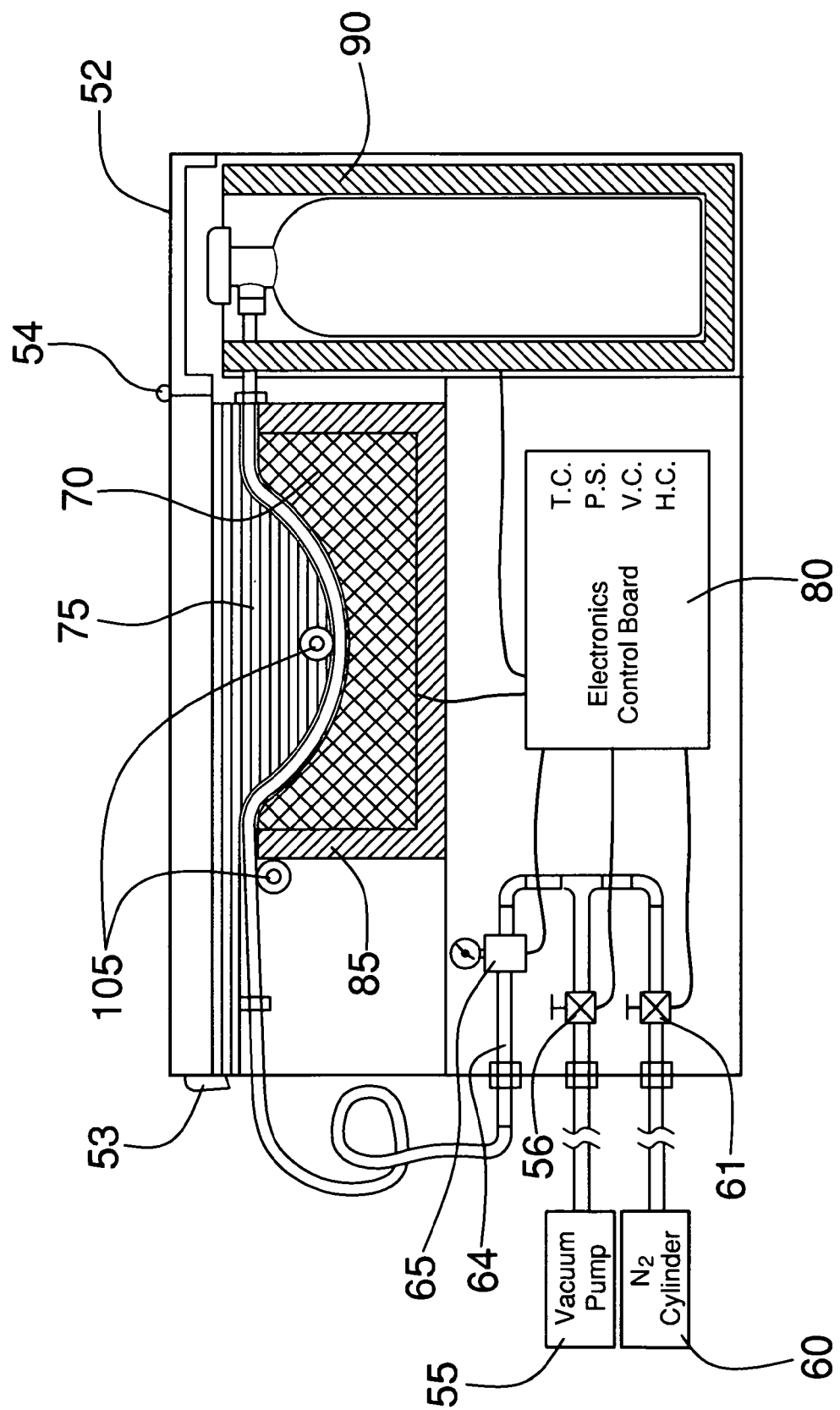
FIG. 6 shows the second embodiment of the preparation station with the first lid in a closed position.
Figure 7:
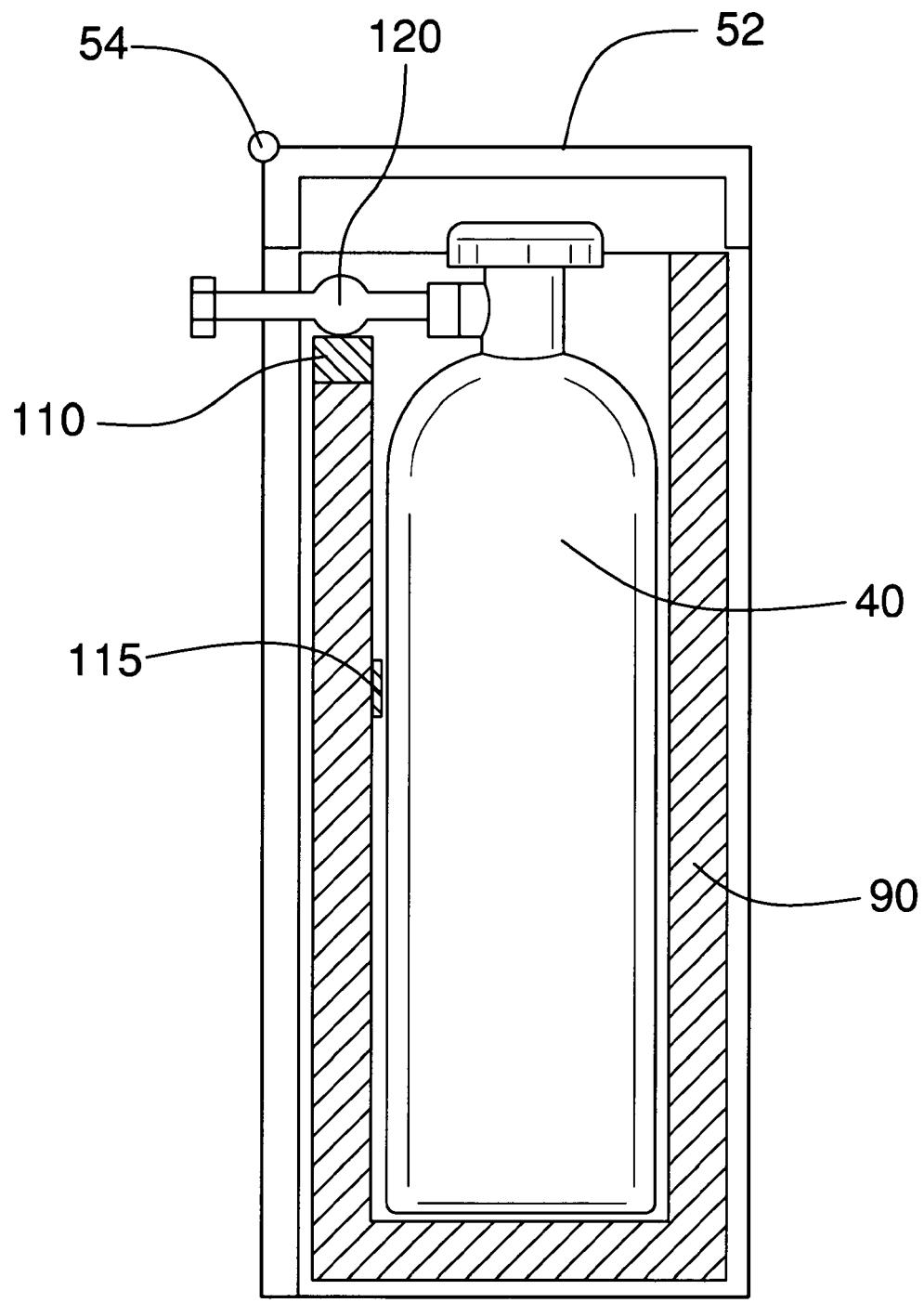
FIG. 7 shows the compartment holding the cylinder having a formed adapter, load sensor and IR sensor.

This second embodiment 100 shares many components of the first embodiment 50, however this second embodiment additionally utilizes a plurality of bearings 105. At least one bearing of the plurality of bearings 105 is placed on the lid mandrel 75 and at least one bearing of the plurality of bearings 105 is placed proximate to the heated mandrel 70, which is shown in FIG. 5 and FIG. 6. The second embodiment 100 also comprises a housing 100A and anticipates providing the flexible gas supply line 66 on the exterior of the housing.

While the embodiments of the invention have been disclosed, certain modifications may be made by those skilled in the art to modify the invention without departing from the spirit of the invention.

The invention claimed is:
1. A gas phase standard preparation device comprising:
  a. a housing;
    wherein the housing has a first lid and a second lid;
    wherein the first lid is hinged to the housing;
    wherein the second lid is hinged to the housing;
  b. a sealed ampule tube;
    wherein the sealed ampule tube is further comprised of an ampule, an ampule sleeve, a plurality of spacers, a first compression fitting, a second compression fitting, a first end, and a second end;
    wherein the ampule is provided within the ampule sleeve;
    wherein the plurality of spacers is provided within the ampule sleeve;
  c. a gas supply line;
    wherein the gas supply line has a first end and a second end;
    wherein the second end of the gas supply line is linked to the first end of the sealed ampule tube:
  d. a pressure sensor;
    wherein the pressure sensor is linked to the first end of the gas supply line;
    wherein the pressure sensor is provided in the housing;
  e. a vacuum pump valve;
    wherein the vacuum pump valve is linked to the pressure sensor;
    wherein the vacuum pump valve is provided in the housing;
  f. a gas valve;
    wherein the gas valve is linked to the pressure sensor;
    wherein the gas valve is provided in the housing;
  g. a mandrel;
    wherein the mandrel provides heating elements;
    wherein the mandrel provides an arcuate surface;
  h. a lid mandrel:
    wherein the lid mandrel is attached to the first lid;
    wherein the lid mandrel provides an arcuate surface;
  i. an electronics control board;
    wherein the electronics control board electronically links to the pressure sensor, the vacuum pump valve, and the gas valve.
2. The gas phase standard preparation device of claim 1 wherein the sealed ampule tube is removable.
3. The gas phase standard preparation device of claim 1 wherein a reference material cylinder is linked to the sealed ampule tube.

4. The gas phase standard preparation device of claim 1 wherein a power source is provided.

5. The gas phase standard preparation device of claim 4 wherein the power source is alternating current mains.

6. The gas phase standard preparation device of claim 4 wherein the power source is a battery.

7. The gas phase standard preparation device of claim 1 wherein the housing provides a plurality of compartments.

8. The gas phase standard preparation device of claim 7 wherein a reference material cylinder is substantially isolated in one of the plurality of compartments.

9. The gas phase standard preparation device of claim 8 wherein the compartment that the reference material cylinder is substantially isolated in includes a bulkhead.

10. The gas phase standard preparation device of claim 3 wherein an IR sensor is provided and is electronically linked to the electronics control board to allow for monitoring the temperature of the reference material cylinder.

11. The gas phase standard preparation device of claim 3 wherein a load sensor is provided and is electronically linked to the electronics control board to allow for monitoring the weight of the reference material cylinder to determine the mass of gas being added.

12. The gas phase standard preparation device of claim 3 wherein a heat sink is provided to provide containment integrity for the reference material cylinder and to prevent overheating of the reference material cylinder.

13. The gas phase standard preparation device of claim 1 wherein insulation walls are provided proximate the mandrel to insulate the mandrel from heat loss.

14. The gas phase standard preparation device of claim 1 wherein the gas valve and vacuum pump valve are proportional valves.

15. The gas phase standard preparation device of claim 1 wherein at least one bearing is provided on the lid mandrel.

16. The gas phase standard preparation device of claim 1 wherein at least one bearing is provided proximate to the mandrel.

17. A method of using a gas phase standard preparation device comprising:
   obtaining the gas phase standard preparation device of claim 3, then;
   a. placing a clean and evacuated reference material cylinder into the housing;
   b. linking the first end of the sealed ampule tube to the gas supply line;
   c. linking the second end of the sealed ampule tube to the reference material cylinder;
   d. evacuating the sealed ampule sleeve;
   e. leak-checking the sealed ampule sleeve;
   f. opening a shutoff valve of the reference material cylinder;
   g. starting a trickle flow of a diluent gas into the gas phase standard preparation device;
   h. closing the first lid;
   i. breaking the ampule and releasing ampule reference material;
   j. starting a preparation program;
   k. filling the reference material cylinder with the diluent gas and the ampule reference material, thereby forming a final reference material; and
   l. closing the shutoff valve of the reference material cylinder.

18. The method of using the gas phase standard preparation device of claim 17 further comprising:
   verifying the concentration of the final reference material within the reference material cylinder.

19. The method of using the gas phase standard preparation device of claim 17 wherein the preparation program further comprising:
   a. heating the mandrel to a predetermined temperature;
   b. flowing diluent gas through the sleeve containing the broken ampule;
   c. monitoring the temperature of the reference material cylinder;
   d. pressurizing the reference material cylinder to a predetermined pressure.

20. The method of using the gas phase standard preparation device of claim 19 further comprising:
   heating the mandrel to a desired temperature up to 240 degrees Celsius.

* * * * *